US005807978A

United States Patent [19]
Kokolus et al.

[11] Patent Number: 5,807,978
[45] Date of Patent: Sep. 15, 1998

[54] IMMUNOGENIC PEPTIDES OF PROSTATE SPECIFIC ANTIGEN

[76] Inventors: William J. Kokolus, 7900 Cambridge St. #14-2L, Houston, Tex. 77054; Herbert A. Fritsche, 4506 Frontier, Houston, Tex. 77041; Dennis A. Johnston, 2010 Ramada Dr., Houston, Tex. 77062

[21] Appl. No.: 472,228

[22] Filed: Jun. 7, 1995

[51] Int. Cl.$^6$ .................. A61K 39/385; A61K 39/39; C07K 7/04; C07K 14/47

[52] U.S. Cl. .................. 530/300; 530/326; 530/327; 530/403; 424/184.1; 424/1.57; 424/185.1; 424/277.1

[58] Field of Search .................. 530/326, 327; 424/184.1

[56] References Cited

U.S. PATENT DOCUMENTS

| | | |
|---|---|---|
| Re. 33,405 | 10/1990 | Chu et al. . |
| 4,172,124 | 10/1979 | Koprowski et al. . |
| 4,331,647 | 5/1982 | Goldenberg . |
| 4,446,122 | 5/1984 | Chu et al. . |
| 4,554,101 | 11/1985 | Hopp . |
| 4,690,890 | 9/1987 | Loor et al. . |
| 5,019,384 | 5/1991 | Gefter et al. . |
| 5,055,404 | 10/1991 | Ueda et al. . |
| 5,153,118 | 10/1992 | Wright, Jr. et al. . |
| 5,221,605 | 6/1993 | Bard et al. . |
| 5,238,808 | 8/1993 | Bard et al. . |
| 5,273,743 | 12/1993 | Ahlem et al. . |
| 5,310,687 | 5/1994 | Bard et al. . |

FOREIGN PATENT DOCUMENTS

| | | |
|---|---|---|
| WO 81/01849 | 7/1981 | WIPO . |
| WO 95/03334 | 2/1995 | WIPO . |
| WO 95/30758 | 11/1995 | WIPO . |

OTHER PUBLICATIONS

Christensson, Eur J. Biochem 220:45 1994.

Alfthan and Stenman, "Falsely Low Results Obtained with the Hybritech Tandem®–R PSA Assay," *Clinical Chemistry*, 34(10):2152, 1988.

Ball et al., "Detailed Mapping of the Antigenicity of the Surface Unit Glycoprotein of Equine Infectious Anemia Virus by Using Synthetic Peptide Strategies," *Journal of Virology*, 66(2):732–742, Feb., 1992.

Bonci et al., "Characterization of immunoreactive octapeptides of human–cytomegalovirus gp58," *Eur. J. Biochem.*, 215:383–387, 1993.

Bridon and Dowell, "Structural Comparison of Prostate–Specific Antigen and Human Glandular Kallikrein Using Molecular Modeling," *Urology*, 45(5): 801–806, May, 1995.

Bruccoleri et al., "Structure of antibody hypervariable loops reproduced by a conformational search algorithm," *Nature*, 335:564–568, Oct., 1988.

Carlacci and Englander, "The Loop Problem in Proteins: A Monte Carlo Simulated Annealing Approach," *Biopolymers*, 33:1271–1286, 1993.

Chan et al., "Prostate–Specific Antigen as a Marker for Prostatic Cancer: a Monoclonal and a Polyclonal Immunoassay Compared," *Clin. Chem.*, 33(10):1916–1920, 1987.

Chou and Fasman, "Empirical Predictions of Protein Conformation," *Ann. Rev. Biochem.*, 47:251–276, 1978.

Chou and Fasman, "Prediction of Protein Conformation," *Biochemistry*, 13(2):222–245, 1974.

Chu et al., "Prostate–Specific Antigenic Domain of Human Prostate Specific Antigen Identified with Monoclonal Antibodies," *The Journal of Urology*, 141:152–156, Jan., 1989.

Corr et al., "Endogenous Peptides of a Soluble Major Histocompatibility Complex Class I Molecule, H–2L$^{d_s}$: Sequence Motif, Quantitative Binding, and Molecular Modeling of the Complex," *The Journal of Experimental Medicine*, 176:1681–1692, Dec., 1992.

Corr et al., "H–2D$^d$ Exploits a Four Residue Peptide Binding Motif," *The Journal of Experimental Medicine*, 178:1877–1892, Dec., 1993.

Das and Lindstrom, "Epitope Mapping of Antibodies to Acetylcholine Receptor α Subunits Using Peptides Synthesized on Polypropylene Pegs," *Biochemistry*, 30:2470–2477, 1991.

Dernick et al., "Detection of Prostate Specific Antigen (PSA) with Monoclonal Antibodies Detected Against Native and Denatured PSA," *In: Journal of Cellular Biochemistry (Abstract)*, Keystone Symposia on Molecular and Cellular Biology, Suppl. 16D, p. 96, Mar., 1992.

Dill et al., "Cooperativity in protein–folding kinetics," *Proc. Natl. Acad. Sci. USA*, 90:1942–1946, Mar., 1993.

Dyson et al., "The immunodominant site of a synthetic immunogen has a conformational preference in water for a type–II reverse turn," *Nature*, 318:480–483, Dec., 1985.

Fasman et al., "Conformational Analysis of the Immunodominant Epitopes of the Curcumsporozoite Protein of *Plasmodium Falciparum* and *knowlesi*," *Biopolymers*, 29:123–130, 1990.

Fetrow and Bryant, "New Programs for Protein Tertiary Structure Prediction," *Bio/Technology*, 11:479–484, Apr., 1993.

Fine et al., "Predicting Antibody Hypervariable Loop Conformations II: Minimization and Molecular Dynamics Studies of MCPC603 From Many Randomly Generated Loop Conformations," *Proteins: Structure, Function, and Genetics*, 1:342–362, 1986.

Graves et al., "Comparison of a Polyclonal and Monoclonal Immunoassay for PSA: Need for An International Antigen Standard," *The Journal of Urology*, 144:1516–1522, Dec., 1990.

(List continued on next page.)

*Primary Examiner*—Toni R. Scheiner
*Assistant Examiner*—Nancy A. Johnson
*Attorney, Agent, or Firm*—Marianne Fuierer; Howard M. Ellis

[57] ABSTRACT

Peptides derived from prostate specific antigen (PSA) that correspond to the immunodominant epitopes found in the native antigen are disclosed. These peptides were identified using a method that predicts continuous, immunodominant epitopes. Anti-PSA antibodies, methods for their production and their use in diagnostic assays also are disclosed.

10 Claims, 1 Drawing Sheet

OTHER PUBLICATIONS

Groneborn and Clore, "Experimental Support for the 'Hydrophobic Zipper' Hypothesis," *Science*, 263:536, Jan., 1994.

Henttu and Vihko, "cDNA Coding for the Entire Human Prostate Specific Antigen Shows High Homologies to the Human Tissue Kallikrein Genes," *Biochemical and Biophysical Research Communications*, 160(2):903–910, Apr., 1989.

Hodges et al., "Antigen–Antibody Interaction," *The Journal of Biological Chemistry*, 263(24):11768–11775, Aug., 1988.

Hofmann et al., "Protein–Water Interaction Energies as Predictor for Antigenic Determinants," *Molecular Immunology*, 27(10):1057–1060, 1990.

Höhne et al., "Structural Base of the Interaction of a Monoclonal Antibody Against p24 of HIV–1 with its Peptide Epitope," *Molecular Immunology*, 30(13):1213–1221, 1993.

Holzmann et al., "Assessment of the antigenic structure of tick–borne encephalitis virus by the use of synthetic peptides," *Journal of General Virology*, 74:2031–2035, 1993.

Jameson and Wolf, "The antigenic index: a novel algorithm for predicting antigenic determinants," *CABIOS*, 4(1):181–186, 1988.

Janin, "Surface and inside volumes in globular proteins," *Nature*, 277:491–492, Feb., 1979.

Javaherian et al., "Principal neutralizing domain of the human immunodeficiency virus type 1 envelope protein," *Proc. Natl. Acad. Sci. USA*, 86:6768–6772, Sep., 1989.

Jurincic–Winkler et al., "Clinical Evaluation of a New Prostate–Specific Antigen Sandwich ELISA Which Employs Four Monoclonal Antibodies Directed at Different Epitopes of Prostate–Specific Antigen," *Eur. Urol.*, 24:487–491, 1993.

Kessler, "Use of Protein A–Bearing Staphylococci for the Immunoprecipitation and Isolation of Antigens from Cells," *Methods in Enzymology*, 73:442–459, 1981.

Kolaskar and Tongaonkar, "A semi–empirical method for prediction of antigenic determinants on protein antigens," *FEBS*, 276(1,2):172–174, Dec., 1990.

Kyte and Doolittle, "A Simple Method for Displaying the Hydropathic Character of Protein," *J. Mol. Biol.*, 157:105–132, 1982.

McCormack et al., "Molecular Forms of Prostate–Specific Antigen and the Human Kallikrein Gene Family: A New Era," *Urology*, 45(5):729–744, May, 1995.

Meek, "Prediction of peptide retention times in high–pressure liquid chromatography on the basis of amino acid composition," *Proc. Natl. Acad. Sci. USA*, 77(3):1632–1636, Mar., 1980.

Pellequer et al., "Correlation between the location of antigenic sites and the prediction of turns in proteins," *Immunology Letters*, 36:83–100, 1993.

Pellequer et al., "Predicting Location of Continuous Epitopes in Proteins from Their Primary Structures," *Methods in Enyzmology*, 203:176–197, 1991.

Ralston et al., "Synthetic Peptides Used To Locate the α–Bungarotoxin Binding Site and Immunogenic Regions on α Subunits of the Nicotinic Acetylcholine Receptor," *Biochemistry*, 26:3261–3266, 1987.

Reddehase et al., "A pentapeptide as minimal antigenic determinant for MHC class I–restricted T lymphocytes," *Nature*, 337:651–653, Feb., 1989.

Regenmortel, "Synthetic Peptides and Monoclonal Antibodies in Immunoassays," *Nucl. Med. Biol.*, 14(4):277–280, 1987.

Regenmortel, "Structural and functional approaches to the study of protein antigenicity," *Immunology Today*, 10(8):266–272, 1989.

Rock et al., "Evaluation of a Monoclonal Immunoradiometric Assay for Prostate–Specific Antigen," *Clinical Chemistry*, 33(12):2257–2261, 1987.

Rothbard and Taylor, "A sequence pattern common to T cell epitopes," *The EMBO Journal*, 7(1):93–100, 1988.

Scott et al., "Mapping the Locations of the Epitopes of Five Monoclonal Antibodies to the Core Protein of Dermatan Sulfate Proteoglycan II (Decorin)," *The Journal of Biological Chemistry*, 268(16):11558–11564, Jun., 1993.

Silverio et al., "New Ultrasensitive Assay Development by Using Monoclonal Antibodies for Detecting Prostate–Specific Antigen," *Eur. Urol.*, 21(supp. 1):79–82, 1992.

Snijders et al., "Identification of linear epitopes on Semliki Forest virus E2 membrane protein and their effectiveness as a synthetic peptide vaccine," *Journal of General Virology*, 72:557–565, 1991.

Suhrbier et al., "Prediction of an HLA B8–restricted influenza epitope by motif," *Immunology*, 79:171–173, May, 1993.

Thole et al., "A Major Immunogenic 36,000–Molecular–Weight Antigen from *Mycobacterium leprae* Contains an Immunoreactive Region of Proline–Rich Repeats," *Infection and Immunity*, 58(1):80–87, Jan., 1990.

Turkes et al., "Prostate–specific Antigen: Protein in Analysis," *J. Eur. J. Cancer*, 27(5):650–652, 1991.

Vessella and Lange, "Issues in the Assessment of PSA Immunoassays," *Urologic Clinics of North America*, 20(4):607–619, Nov., 1993.

Wolf et al., "An integrated family of amino acid sequence anaylsis programs," *CABIOS*, 4(1):187–191, 1988.

Wright, Jr. et al., "Generation and Characterization of Monoclonal Antibodies to Prostate Secretory Protein," *Int. J. Cancer*, 46:39–49, 1990.

Zhou et al., "Multiple Forms of Prostate–Specific Antigen in Serum: Differences in Immunorecognition by Monoclonal and Polyclonal Assays," *Clin. Chem.*, 39(12):2483–2491, 1993.

Martin–Moe et al., "Hydrophobic Interactions and the Design of Receptor Mimetic Peptides," *Peptide Research*, 8(2):70–76, 1995.

Takayama et al., "A Brief Review of Ultrasensitive Prostate–Specific Antigen Assays for the Evaluation of Patients After Radical Prostatectomy," *World J. Urol.*, 11:192–195, 1993.

Zvi et al., "The Principal Neutralizing Determinant of HIV–1 Located in V3 of gp120 Forms a 12–Residue Lop by Internal Hydrophobic Interactions," *FEBS Letters*, 368:267–270, 1995.

Ausubel et al., Current Protocols in Molecular Biology, vol. 2, publ. Greene Publishing Associates and Wiley–Interscience, 11.14.1–11.15.4, 1989.

Bander, "Current Status of Monoclonal Antibodies for Imaging and Therapy of Prostate Cancer"; *Seminars in Oncology*, 21:5, 607–612, 1994.

Leroy et al., "Radioimmunodetection of Lymph Node Invasion in Prostatic Cancer", *Cancer*, 64:1–5, 1989.

Lundwall et al., "Molecular Cloning of Human Prostate Specific Antigen cDNA", *FEBS Letters*, 214:2, 317–322, 1987.

Palfreyman, et al., "Guidelines for the Production of Polypeptide Specific Antisera Using Small Synthetic Oligopeptides as Immunogens", *Journal of Immunological Methods*, 75:383–393, 1984.

Sela, "Synthetic Approaches to Applied Medical Aspects of Immunology", *Asian Journal of Infectious Diseases*, 1:97–103, 1977.

```
Ile Val Gly Gly Trp Glu Cys Glu Lys His Ser Gln Pro Trp
Gln Val Leu Val Ala Ser Arg Gly Arg Ala Val Cys Gly Gly
Val Leu Val His Pro Gln Trp Val Leu Thr Ala Ala His Cys
Ile Arg Arg Lys Ser Val Ile Leu Leu Gly Arg His Ser Leu
Phe His Pro Glu Asp Thr Gly Gln Val Phe Gln Val Ser Thr
Ser Phe Pro His Pro Leu Tyr Asp Met Ser Leu Leu Lys Asn
Arg Phe Leu Arg Pro Gly Asp Asp Ser Ser His Asp Leu Met
Leu Leu Arg Leu Ser Glu Pro Ala Glu Leu Thr Asp Ala Val
Lys Val Met Asp Leu Pro Thr Gln Glu Pro Ala Leu Gly Thr
Thr Cys Tyr Ala Ser Gly Trp Gly Ser Ile Glu Pro Glu Glu
His Leu Leu Tyr Asp Gln Met Lys Lys Leu Gln Cys Val Gln
Leu His Val Ile Ser Asn Asp Val Cys Ala Gln Val His Pro
Gln Lys Val Thr Lys Phe Met Leu Cys Ala Gly Arg Trp Thr
Gly Gly Lys Ser Thr Cys Ser Gly Asp Ser Gly Gly Pro Leu
Val Cys Asn Gly Val Leu Gln Gly Ile Thr Ser Trp Gly Ser
Glu Pro Cys Ala Leu Pro Glu Arg Pro Ser Leu Tyr Thr Lys
Val Val His Tyr Arg Lys Trp Ile Lys Asp Thr Ile Val Ala
Asn Pro
```

FIG. 1

IMMUNOGENIC PEPTIDES OF PROSTATE SPECIFIC ANTIGEN

I. FIELD OF THE INVENTION

The invention relates generally to the field of cancer diagnosis. More particularly, there is described an immunological method, and accompanying reagents, for the production of antibodies useful in the diagnosis of prostate cancer.

II. BACKGROUND OF THE INVENTION

Prostate cancer is prevalent in old age, with approximately one-half of all males over the age of 70 having been shown to develop prostatic cancer. This high incidence rate has led to the search for markers that may be useful in the detection of prostate malignancy. For example, serum acid phosphatase activity is elevated in patients having metastasized prostate carcinoma. Gutman et al., *J. Clin. Invest.* 17:473 (1938). Numerous studies of this enzyme and its relation to prostatic cancer have been made, but attempts to develop a specific test for prostatic acid phosphatase have met with only limited success. One problem is that there are difficulties associated with accounting for biological and immunological activity of unrelated phosphatases. Immunologic assays suffer additional limitations in terms of sensitivity.

Prostate specific antigen, or PSA, has been studied as another possible serum marker for prostatic cancer. The serum concentrations of PSA correlate with the clinical stage of prostatic cancer in untreated patients and are increased in 86% of patients with benign prostatic hyperplasia. PSA, also characterized independently as seminal plasma protein p30 (Sensabaugh and Blake, *J. Urol.* (UNITED STATES) Dec. 1990, 144 (6) p 1523–6) or as [γ]-seminoprotein, (Hara and Kimura, *J. Lab. Clin. Med.* (UNITED STATES) May 1989, 113 (5) p541–8), is a glycoprotein of 33–34 kDa. PSA is synthesized in, and secreted by, the epithelial cells of the prostate gland. It belongs to the group serine proteases, and the high molecular weight seminal vesicle protein of seminal coagulates is thought to be its normal biological substrate. Elucidation of the amino acid sequence of mature human PSA by sequencing of the protein and corresponding cDNA showed that PSA closely resembles many murine and human proteases of the kallikrein family.

Testing for PSA expression has become an important methods in diagnosing and managing prostate cancer. The test is widely used, along with digital rectal examination and diagnostic ultrasonography, to permit an early diagnosis of prostate cancer in high-risk men. After radical prostatectomy, a fall in the serum PSA concentration to undetectable levels gives assurance of curative therapy, while measurable PSA concentrations which persist after surgery indicate the existence of extra-capsular disease and the need for additional therapy. Serial PSA monitoring of patients after curative therapy can identify patients who develop recurrent disease, in many cases long before clinical symptoms are evident.

Because of its potential as a diagnostic marker for human prostate cancer, it will be of interest to develop immunologic reagents capable of reacting specifically with PSA. In light of the structural relationship between PSA and other molecules, however, it appears that it will be necessary to generate antibodies against fragments of PSA, rather than against the entire molecule. Fragments can be generated by proteolytic cleavage but, because the sequence of PSA is known, it also is possible to chemically synthesize oligopeptides of interest.

Unfortunately, the ability of a given oligopeptide to elicit antibody responses that cross-react with the native molecule currently is unpredictable at best. One reason is that oligopeptides only have the ability to represent linear or "continuous" epitopes. "Discontinuous" epitopes are composed of sequences from throughout an antigen and rely on folding of the protein to bring the sequences into close proximity of one another. Clearly, oligopeptides are incapable of representing such epitopes. Moreover, even though continuous epitopes are structurally less complicated than discontinuous ones, there remains only a poor understanding of how the immune system recognizes and responds to these antigenic species.

The foregoing limitations are significant in that the clinical accuracy of a immunodiagnostic PSA assay is related to the specificity and sensitivity of the test procedure. Recently, it has been demonstrated that the existing monoclonal antibodies and polyclonal antisera used for current PSA assays cross-react with HgK-1. This raises serious questions regarding the accuracy of these tests and highlights the importance of developing more selective reagents for this kind of assay.

Unfortunately, the ability to predict which portions of a given antigen reflect epitopes presently is limited. On the other hand, random screening of oligopeptides to determine potential immunogens is a time-consuming and expensive endeavor that is impractical with even moderately-sized polypeptides. Thus, the identification of immunologic oligopeptides of PSA suitable for use in the development of PSA-specific antibodies is of paramount importance.

III. SUMMARY OF THE INVENTION

Therefore, it is an object of the present invention to provide a panel of immunodominant peptides suitable for the generation of antibodies to PSA. It also is an object of the present invention to provide compositions including immunodominant PSA peptides suitable for the immunization of animals. It is yet another object of the present invention to provide methods for the generation of polyclonal and monoclonal antibodies reactive with PSA peptides and to PSA itself.

In fulfilling these objects, there is provided a peptide of twelve to twenty-one contiguous amino acid residues from the sequence of PSA, wherein said peptide is defined by a motif of about twelve to twenty-one amino acid residues in length having two hydrophobic and one hydrophilic regions arranged in the following manner:

hydrophobic-hydrophilic-hydrophobic wherein each of said hydrophobic and hydrophilic regions are of about five amino acid residues in length. In one embodiment, the motif further is defined by a proline residue (i) within said hydrophilic region, (ii) at the border of said hydrophilic region or (iii) at least five amino acid residues from one end of said peptide. In another embodiment, the peptide further comprises a leucine, isoleucine or lysine residue within one or both of said hydrophobic regions. In yet another embodiment, the peptide further is characterized by an approximated 360° (−)cosine hydrophilicity pattern.

In a particular embodiment, the peptide corresponds to the twenty-one N- or C-terminal residues of the sequence of PSA. In other particular embodiments, the amino acid sequence of the peptide is selected from the group consisting of LYTKVVHYRKWIKDTIVANP(SEQ ID NO:2), AVKVMDLPQEPALGTTCYA(SEQ ID NO:3), IVGGWECEKHSQPWQVLVAS(SEQ ID NO:4), CAQVHPQKVTKFML(SEQ ID NO:5), YLMLLRLSEPAELTDDAVKVM(SEQ ID NO:6), LLKNRFLRPGDDSSHDLMLLY(SEQ ID NO:7), and ILLGRHSLFHPEDTGQVFQVY(SEQ ID NO:8). A preferred embodiment is a peptide having the sequence CAQVHPQKVTKFML(SEQ ID NO:5). Also included within the invention are variants of peptides having the above amino acid sequence where the variant have one, two, three, four or five residues that are conservative variations of the selected sequence.

Also provided are antigenic compositions comprising any of the foregoing peptides and a carrier molecule and/or an adjuvant.

There also is provided a polyclonal antisera specific for a peptide of twelve to twenty-one contiguous amino acid residues from the sequence of PSA, wherein said peptide is defined by a motif of about twelve to twenty-one amino acid residues in length having two hydrophobic and one hydrophilic regions arranged in the following manner:

hydrophobic-hydrophilic-hydrophobic wherein each of said hydrophobic and hydrophilic regions are of about five amino acid residues in length. In another embodiment, the motif further is defined by a proline residue (i) within said hydrophilic region, (ii) at the border of said hydrophilic region or (iii) at least five amino acid residues from one end of said peptide. A preferred antisera is specific for CAQVHPQKVTKFML(SEQ ID NO:5).

There also is provided a polyclonal antisera generated by immunization of an animal with a peptide of twelve to twenty-one contiguous amino acid residues from the sequence of PSA, wherein said peptide is defined by a motif of about twelve to twenty-one amino acid residues in length having two hydrophobic and one hydrophilic regions arranged in the following manner:

hydrophobic-hydrophilic-hydrophobic wherein each of said hydrophobic and hydrophilic regions are of about five amino acid residues in length. In another embodiment, at least 80% of the antibodies of said antisera bind to the same determinant of said peptide. A preferred embodiment is a peptide with the sequence CAQVHPQKVTKFML(SEQ ID NO:5).

There also is provided a method for diagnosing prostate cancer comprising the steps of (i) providing a sample; (ii) contacting said sample with antisera specific for a peptide as defined above; and (iii) detecting the binding said antibody to a polypeptide in said sample. In one embodiment, the method is practiced in vivo. Alternatively, the method can be practiced in vitro. In another embodiment, the antisera is a polyclonal antisera. In yet another embodiment, the method is an ELISA.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

IV. BRIEF DESCRIPTION OF THE DRAWINGS

FIG. 1. The amino acid sequence for PSA is shown(SEQ ID NO:1).

V. DETAILED DESCRIPTION OF THE INVENTION

Because PSA is a potential target for diagnosing prostate cancer, the development of immunologic reagents for the identification of PSA is of considerable interest to both patients and clinicians. As stated above, PSA bears a striking homology to certain kallikreins and, therefore, a significant chance for cross-reactivity with non-PSA antigens exists. In order to generate PSA specific antibodies, it will be necessary to use fragments of PSA and, in all probability, relatively short peptides that represent sequences unique to PSA. A significant body of literature exists, however, indicating that a randomly selected oligopeptide from within a larger polypeptide molecule only rarely elicits a high titer, high affinity antibody response that reacts with the native molecule.

Using a novel method for analyzing the immunogenicity of polypeptides, the present inventors were able to identify fourteen putative continuous epitopes in PSA. Seven of these epitopes were identified as meeting criteria favorable for immunologic reactivity. Peptides representing these epitopes reacted more strongly with polyclonal antisera than did peptides representing the remaining seven epitopes. In addition, three existing monoclonal antibodies were found to recognize two of the seven immunodominant epitopes, thus confirming the importance of these epitopes and the significance of the model.

An Immunologic Model for Identifying Linear Epitopes

One embodiment of the present invention involves the identification of immunologic epitopes within PSA. To select PSA peptides for further analysis, the present inventors developed a method for the identification of immunodominant epitopes within polypeptides. The method is premised on the notion that linear epitopes are defined by two "descriptors." The first descriptor is a continuous sequence of approximately twelve to twenty-one amino acids that forms a "relative" hydrophobic-hydrophilic-hydrophobic motif, with each of these three charged regions containing about five amino acids. By "relative," it is meant that there need not be absolute hydrophobicity or hydrophilicity as defined by classic hydrophobicity or hydrophilicity determinations but, rather, that the regions be hydrophobic or hydrophilic with respect to each other and to the flanking sequences.

The second descriptor is a proline residue at one of the hydrophilic-hydrophobic borders or within the hydrophilic region. When a portion of an antigen contains both of these descriptors, it is expected to represent a particularly immunogenic portion of the molecule. As a general proposition, N- and C-terminal peptides having the first, but not the second descriptor, also are considered to be promising epitopes.

A series of rules are applied as follows. First, potential epitopes are identified by locating every proline residue within the polypeptide. Second, roughly twenty-one amino acid "arrays" are defined for each proline, where the proline is placed at the 11th residue of the 21-mer. Third, all non-overlapping arrays are identified. Fourth, a relative hydrophilic or hydrophobic label is assigned to each residue within the unique arrays according to the method of Jainin, *Nature* 277: 491–492 (1979). Hydrophobic-hydrophilic-hydrophobic patterns are identified where the proline falls within one of the relatively hydrophilic regions. Arrays thus identified have a high probability of representing immunogenic epitopes.

In addition, it may prove useful to further rank the epitopes identified according to the above-noted rules. For example, it is considered even more desirable that the hydrophobic region contain a leucine, isoleucine or lysine.

Another positive indicator of immunodominance is an approximated 360° (−)cosine pattern resulting from a Kyte-Doolittle (1982) hydrophilicity plot. Abramowitz and Stegun, Eds., *HANDBOOK OF MATHEMATICAL FUNCTIONS WITH FORMULAS, GRAPHS AND MATHEMATICAL TABLES*, National Bureau of Standards and Applied Mathematics, Series #55, June 1964, p. 71–79. The specific definition of the negative cosine curve was as provided in the Microsoft Fortran Library, version 5.1 or PC's. The Kyte-Doolittle measurement scale assigns a hydropathy score to each natural amino acid based on side chain (i) interior-exterior distribution and (ii) water-vapor transfer free energy as determined by water-vapor partition coefficients. The values are average over a 5–7 residue window and a value assigned to each window.

Peptides of PSA

The cDNA for PSA predicts a 362 amino acid prepropro-tein. This form contains two cleaved sequences not present in the mature molecule. The first is a seventeen amino acid hydrophobic leader sequence and the second is a seven amino acid "pro" sequence. Thus, the mature molecule is 238 amino acids, with the first amino acid of the mature protein being the twenty-fifth predicted from the cDNA.

As described in the examples, PSA was divided into 14 peptides ranging in size from 16 to 21 amino acids for the initial analysis. For purposes of the present invention, the epitopes defined in PSA will be 12 to 25 amino acids in length. Antibodies will bind a peptide epitope having an immunodominant epitope motif defined by an adjacent hydrophobic, hydrophilic, and hydrophobic region with a proline in the hydrophilic region.

The PSA peptides identified in this application may be modified for particular purposes according to methods well known to those of skill in the art. For example, particular peptide residues may be derivatized or chemically modified in order to alter the immune response or to permit coupling of the peptide to other agents. It also is possible to change particular amino acids within the peptides without disturbing the overall structure or antigenicity of the peptide. Such changes are therefore termed "conservative" changes and tend to rely on the hydrophilicity or polarity of the residue. The size and/or charge of the side chains also are relevant factors in determining which substitutions are conservative.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Particular embodiments encompass variants that have one, two, three, four, five or more variations in the peptides sequence. Of course, a plurality of distinct proteins/peptides with different substitutions may easily be made and used in accordance with the invention.

An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

The hydropathic index of amino acids also may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, *J. Mol. Biol.* 157:105–132, 1982). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biological functional equivalent protein or peptide thereby created is intended for use in immunological embodiments, as in the present case. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

Having identified peptidyl compounds suitable for use as immunogens, it also is contemplated that other sterically similar compounds may be formulated to mimic the key portions of the peptide structure. Such compounds, which may be termed peptidomimetics, may be used in the same manner as the peptides of the invention and hence are also functional equivalents. The generation of a structural functional equivalent may be achieved by the techniques of modeling and chemical design known to those of skill in the art. It will be understood that all such sterically similar constructs fall within the scope of the present invention.

Another method for determining the "equivalence" of modified peptides involves a functional approach. For example, a given peptide can be used to generate monoclonal or polyclonal antibodies. These antibodies can then, in turn, be used to screen libraries of degenerate peptides that include thousand or hundreds of thousands of other peptides, thereby identifying structures that are, at least to a certain extent, immunologically equivalent. Of course, these structures may bear some primary sequence homology to the peptide used to generate the antibodies, but they also may be quite different.

Other Antigens as Sources for Peptides

In theory the application of the immunological model described above could be applied to practically any polypeptide. Some examples are provided below:

Lymphokines and Interferons: IL-1, IL-2, IL-3, IL-4, IL-5, IL-6, IL-7, IL-8, IL-9, IL-10, IL-11, IL-12, IFN-α, IFN-β, IFN-γ.

Cluster Differentiation Antigens and MHC Antigens: CD2, CD3, CD4, CD5, CD8, CD11a, CD11b, CD11c, CD16, CD18, CD21, CD28, CD32, CD34, CD35, CD40, CD44, CD45, CD54, CD56, K2, K1, Pβ, Oα, Mα, Mβ2, Mβ1, LMP1, TAP2, LMP7, TAP1, Oβ, IAβ, IAα, IEβ, IEβ2, IEα, CYP21, C4B, CYP21P, C4A, Bf, C2, HSP, G7a/b, TNF-α, TNF-62, D, L, Qa, Tla, COL11A2, DPβ2, DPα2, DPβ1, DPα1, DNα, DMα, DMβ, LMP2, TAP1, LMP7, DOβ, DQβ2, DQβ2, DQβ3, DQβ1, DQα1, DRβ, DRα, HSP-70, HLA-B, HLA-C, HLA-X, HLA-E, HLA-J, HLA-A, HLA-H, HLA-G, HLA-F.

Hormones and Growth Factors: nerve growth factor, somatotropin, somatomedins, parathormone, FSH, LH, EGF, TSH, THS-releasing factor, HGH, GRHR, PDGF, IGF-I, IGF-II, TGF-β, GM-CSF, M-CSF, G-CSF, erythropoetin.

Tumor Markers and Tumor Suppressors: β-HCG, 4-N-acetylgalactosaminyltransferase, GM2, GD2, GD3, MAGE-1, MAGE-2, MAGE-3, MUC-1, MUC-2, MUC-3, MUC-4, MUC-18, ICAM-1, C-CAM, V-CAM, ELAM, NM23, EGFR, E-cadherin, N-CAM, CEA, DCC, PSA, Her2-neu, UTAA, melanoma antigen p75, K19, HKer 8, pMel 17, tyrosinase related proteins 1 and 2, p97, p53, RB, APC, DCC, NF-1, NF-2, WT-1, MEN-I, MEN-II, BRCA1, VHL, FCC and MCC.

Oncogenes: ras, myc, neu, raf, erb, src, fms, jun, trk, ret, gsp, hst, bcl and abl.

Complement Cascade Proteins and Receptors: C1q, C1r, C1s, C4, C2, Factor D, Factor B, properdin, C3, C5, C6, C7, C8, C9, C1Inh, Factor H, C4b-binding protein, DAF, membrane cofactor protein, anaphylatoxin inactivator S protein, HRF, MIRL, CR1, CR2, CR3, CR4, C3a/C4a receptor, C5a receptor.

Viral Antigens: HIV (gag, pol, gp41, gp120, vif, tat, rev, nef, vpr, vpu, vpx), HSV (ribonucleotide reductase, α-TIF, ICP4, ICP8, ICP35, LAT-related proteins, gB, gC, gD, gE, gH, gI, gJ), influenza (hemagluttinin, neuraminidase, PB1, PB2, PA, NP, $M_1$, $M_2$, $NS_1$, $NS_2$), papillomaviruses (E1, E2, E3, E4, E5a, E5b, E6, E7, E8, L1, L2) adenovirus (E1A, E1B, E2, E3, E4, E5, L1, L2, L3, L4, L5), Epstein-Barr Virus (EBNA), Hepatitis B Virus ($gp27^s$, $gp36^s$, $gp42^s$, $p22^c$, pol, x)

Nuclear Matrix Proteins.

Immunodominant Motif

The hydrophilic region as a defining characteristic of epitope motifs in proteins has been accepted for some time. Such an epitope's hydrophilic amino acids are generally thought to be important in that they situate the epitope on the external portion of the antigen. The present invention contemplates a more complex site having hydrophobic-hydrophilic-hydrophobic structure including at least one proline. Like the simpler model, hydrophilic interactions probably provide some structural features and ensure localization of the epitope on the external portion of the antigen. The flanking hydrophobic interactions at both ends of the hydrophilic region may help dock the epitope in the antibody binding site. The bend in the amino acid sequence at proline may provide a rudimentary, but easily recognizable three-dimensional structure that facilitates the transition from hydrophilic amino acids regions in the complete epitope of a protein.

An antibody's binding to a complete peptide epitope would theoretically enable the epitope to occupy the entire space within an antibody binding site as predicted by X-ray crystallographic studies. This most efficient use of all the amino acids in an epitope would result in the maximization of the available free energy for bond formation and account for the relatively high affinity of binding manifested in antibody-epitope interactions.

A relevant observation regarding this motif was provided in a literature report about an antibody epitope to the alpha subunit of the acetylcholine receptor from Torpedo californica electric organ (*Biochemistry* 30:2470–2477, 1991). The authors observed that the relatively hydrophilic peptide NPDVK(SEQ ID NO:9) from the receptor could not bind antibody alone. Rather, binding occurred only after the addition of either the hydrophobic LI amino acids to the amino-terminus or the hydrophobic AI amino acids to the carboxy-terminus, suggesting the importance of a hydrophobic binding region occurring on either side of the middle region. These findings are consistent with three partial epitopes—hydrophobic-hydrophilic-hydrophilic-proposed here.

Rabbit antiserum was produced to the 14 mer peptide TINKEDDESPGLYG(SEQ ID NO:10) linked to keyhole limpet hemocyanin. In a competitive ELISA, the affinity of the antiserum antibody population that binds to TINKED (SEQ ID NO:11) is the same for the 5 mer peptide TINKE (SEQ ID NO:12) as for the 11 mer TINKEDDESPG(SEQ ID NO:13). Also in an ELISA, the antiserum does not bind to the peptide NKEDDES(SEQ ID NO:14), but the 3 mer TIN partially inhibits the binding of the antiserum to TINKED(SEQ ID NO:11). Thus, from the 14 mer, the isolated hydrophilic amino acids NKEDDES(SEQ ID NO:14) could not bind antibodies alone but one or both of the amino acids T and I, most likely I, is important in anchoring the N-terminus of the epitope to an antibody binding site.

In a competitive ELISA, the affinity of the antisera that binds to TINKED(SEQ ID NO:11) is greater for the 14 mer TINKEDDESPGLYG(SEQ ID NO:10) than for the 11 mer TINKEDDESPG(SEQ ID NO:11). Thus, it is apparent that the epitope defined by this antisera also requires at least one of the C-terminal hydrophobic amino acids, L, Y or G, for its complete expression.

When the sequence order of the amino acids in this epitopic region was inverted, other similarities with the peptide TINKEDDESPGLYG(SEQ ID NO:10), immunochemically characterized above, were noted:

T I N K E D D E S P G L Y G(SEQ ID NO:10)

V G E I A S K V D P N K I L(SEQ ID NO:15)

Both epitopes had relatively hydrophobic termini with leucine and/or isoleucine also present, indicating the possibility of a ubiquitous hydrophobic binding mechanism occurring in the termini. The lysine relative to isoleucine also may be implicated. The possible existence of such a "hydrophobic zipper" binding mechanism with leucines playing a major role has been proposed recently to be important in protein folding dynamics (*Proc. Nat'l Acad. Sci. USA* 90:1953, 1993*; Science* 263:536, 1994). The middle sections in both of these examples are relatively hydrophilic, do not bind antibody by themselves, and a proline is located at the border within the relatively hydrophilic region of the peptide in both, although the sequence order is from the C-terminal to N-terminal in the lower example. Hydrogen bonding utilizing the middle hydrophilic amino acids may play a significant role in determining epitope specificity, even though not contributing greatly to the overall strength of the antibody-epitope bond.

Known antibody epitopes ascribed to four proteins reported in the scientific literature were evaluated for their correspondence with the proline and hydrophobic-hydrophilic-hydrophobic immunodominant epitope motif. The motif was used to successfully locate immunodominant and neutralizing antibody epitopes for the following:

a) The three most immunodominant epitopes from the 437 amino acid equine infectious anemia virus surface unit glycoprotein gp90 (J. Virol. 66:732–742, 1992) were predicted. The dual motifs model actually predicted four immunodominant regions. The fourth predicted region was not tested for in the published study.

b) The single neutralization epitope for the four hundred and twenty-four amino acid Semliki Forest virus E2 membrane protein (J. Gen. Virol. 72:557–565, 1991) matched one of the seven sites predicted by the model.

c) The major immunodominant epitope mapped in human cytomegalovirus glycoprotein gp58 (Eur. J. Biochem. 215:383–387, 1993) was one of two sites predicted by the model in the eighty-three amino acid region of the protein that was thought to contain this epitope.

d) The epitope recognized by one of two monoclonal antibodies elicited against the 500 amino acid tick-borne encephalitis envelope protein E also was located (J. Gen. Virol. 74:2031–2035, 1993) by this method. The epitope for the other monoclonal antibody was mapped to the N-terminal region of the protein. This site contained neither a proline or hydrophobic-hydrophilic-hydrophobic motif, but as previously indicated, the N and C-terminal regions may nonetheless elicit an antibody response due to their high mobility and accessibility. Although not tested with polyclonal antiserum, the model predicted eleven possible immunodominant regions in this protein.

These findings provide strong evidence that the proposed motif is an indicator of immunologic significance in antigens.

The immunodominant motif identifies regions in various proteins that elicit high titer antibody responses because it defines loop or pseudo-loop structures in proteins known to elicit high titer functional antibodies in proteins such as HIV-1 gp120. It is hypothesized that some mutated epitopes have become immunologically dysfunctional due to their having a disrupted immunodominant motif pattern. In light of the present disclosure, it is now possible to bioengineer replacement epitopes capable of eliciting a functional immune response directed towards predicted mutated protein epitopes. It will be appreciated by those in the field that these new epitopes will have numerous applications in microbial and cancer vaccinology, therapy and diagnosis.

Antigen Compositions, Adjuvants and Methods of Immunization

In order to develop anti-PSA immunologic reagents, it is contemplated that the peptides identified above will be used in the form of antigen compositions for the immunization of animals. Even though some oligopeptides may be immunogenic in and of themselves, it often will be desirable to conjugate oligopeptides to higher molecular weight carrier molecules. Two common carrier molecules are bovine serum albumin (BSA) and keyhole limpet hemocyanin (KLH). Other albumins such as ovalbumin, mouse serum albumin or rabbit serum albumin also can be used as carriers. Synthetic carriers also are used and are readily available. Means for conjugating a polypeptide to a carrier protein are also well known in the art and include glutaraldehyde, m-maleimidobencoyl-N-hydroxysuccinimide ester, carbodiimide and bis-biazotized benzidine.

A variety of different PSA immunogens can be used to produce monoclonal antibodies according to the present invention. For example, peptides may be chemically-synthesized, based on the identified PSA sequences. In certain cases, it may be desirable to link several PSA epitopes together in a single immunogen. Again, these immunogens can be synthesized chemically, either as a single molecule or separately followed by conjugation. With larger peptides, it may prove more practical to create synthetic genes and express the corresponding protein in a host cell (e.g., a bacterial, insect, yeast or mammalian cell). Transformation of host cells may be either transient or stable. Stable transformation may be achieved by either integration into the host genome or by episomal maintenance of an expression vector. Bacterial hosts are desired where post-translational modifications of the protein to be produced are minimal. Where post-translational modifications are significant, it may be necessary to use eukaryotic hosts such as insect, yeast, mammalian or even human cells.

In certain situations, it will be desirable to provide adjuvants that enhance the immune response to PSA peptides. Such adjuvants include all acceptable immunostimulatory compounds such as cytokines, toxins or synthetic compositions. Examples of these are IL-1, IL-2, BCG, aluminum hydroxide, N-acetyl-muramyl-L-threonyl-D-isoglutamine (thur-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 1983A, referred to as MTP-PE), lipid A, MPL and RIBI, which contains three components extracted from bacteria, monophosphoryl lipid A, trehalose dimycolate and cell wall skeleton (MPL+TDM+CWS) in a 2% squalene/Tween 80 emulsion. Liposomes also can be used as adjuvants.

In addition to adjuvants, it may be desirable to coadminister biologic response modifiers (BRM), which have been shown to downregulate suppressor cell activity. Such BRM's include, but are not limited to, Cimetidine (CIM; 1200 mg/d) (Smith/Kline, Pa.); Indomethacin (IND; 150 mg/d) (Lederle, N.J.); or low-dose Cyclophosphamide (CYP; 75, 150 or 300 mg/m$^2$) (Johnson/Mead, N.J.).

Antigen compositions of the present invention include PSA antigens advantageously administered in the form of injectable, pharmaceutical compositions. A typical composition for such purpose comprises a pharmaceutically acceptable carrier. For instance, the composition may contain about 10 mg of human serum albumin and from about 20 to 200 micrograms of the labeled monoclonal antibody or fragment thereof per milliliter of phosphate buffer containing NaCl. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial, anti-oxidants, chelating agents and inert gases. The pH and exact concentration of the various components the pharmaceutical composition are adjusted according to routine skills in the art.

Antibodies and Antibody Production

As stated above, one of the uses for PSA peptides according to the present invention is to generate antibodies. Reference to antibodies throughout the specification includes whole polyclonal and monoclonal antibodies, and parts thereof, either alone or conjugated with other moieties. Antibody parts include Fab and $F(ab)_2$ fragments and single chain antibodies. The antibodies may be made in vivo in suitable laboratory animals or in vitro using recombinant DNA techniques.

Means for preparing and characterizing antibodies are well known in the art. See, e.g., *ANTIBODIES: A LABORATORY MANUAL*, Cold Spring Harbor Laboratory, 1988 (incorporated herein by reference). The methods for generating polyclonal antibodies are well known in the art. Briefly, polyclonal antisera is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig, a goat, a sheep or a chicken. Because of the relatively large blood volume of rabbits, a rabbit is a preferred choice for production of polyclonal antibodies.

The amount of immunogen composition used in the production of polyclonal antibodies varies upon the nature of the immunogen, as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs (below).

One of the important features provided by the present invention is a polyclonal sera that is relatively homogenous with respect to the specificity of the antibodies therein. Typically, polyclonal antisera is derived from a variety of different "clones," i.e., B-cells of different lineage. Monoclonal antibodies, by contrast, are defined as coming from antibody-producing cells with a common B-cell ancestor, hence their "mono" clonality.

When peptides are used as antigens to raise polyclonal sera, one would expect considerably less variation in the clonal nature of the sera than if a whole antigen were employed. Unfortunately, if incomplete fragments of an epitope are presented, the peptide may very well assume multiple (and probably non-native) conformations. As a result, even short peptides can produce polyclonal antisera with relatively plural specificities and, unfortunately, an antisera that does not react or reacts poorly with the native molecule.

Polyclonal antisera according to present invention is produced against peptides that are predicted to comprise whole, intact epitopes. It is believed that these epitopes are, therefore, more stable in an immunologic sense and thus express a more consistent immunologic target for the immune system. Under this model, the number of potential B-cell clones that will respond to this peptide is considerably smaller and, hence, the homogeneity of the resulting sera will be higher. In various embodiments, the present invention provides for polyclonal antisera where the clonality, i.e., the percentage of clone reacting with the same molecular determinant, is at least 80%. Even higher clonality—90%, 95% or greater—is contemplated.

Anti-PSA antisera or monoclonal antibodies can be identified in a fairly straightforward manner using any one of variety of immunological screening assays in which antibody competition can be assessed. For example, test antibodies can be used in simple competition assays. A known antibody preparation and the test antibody are premixed, incubated with the antigen composition and compete for binding to the PSA peptide. "Antigen composition" means any composition that contains some version of PSA, whole or fragment, in an accessible form. Antigen-coated wells of an ELISA plate are particularly preferred.

In one embodiment, one would pre-mix the known antibodies with varying amounts of the test antibodies (e.g., 1:1, 1:10 and 1:100) for a period of time prior to applying to the antigen composition. If one of the known antibodies is labeled, direct detection of the label bound to the antigen is possible; comparison to an unmixed sample assay will determine competition by the test antibody and, hence, cross-reactivity. Alternatively, using secondary antibodies specific for either the known or test antibody, one will be able to determine competition.

Antibody competition assays are particularly suitable for use in an ELISA or RIA microtiter well format, but any immunoassay may be used. Most preferably, the assay will be capable of generating quantitative results. An antibody that binds to the antigen composition will be able to effectively compete for binding of the known antibody and thus will significantly reduce binding of the latter. The reactivity of the known antibodies in the absence of any test antibody is the control. A significant reduction in reactivity in the presence of a test antibody is indicative of a test antibody that binds to the PSA peptide, i.e., one that "cross-reacts" with the known antibody.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., purified or partially purified protein, synthetic protein or fragments thereof. The immunizing composition is administered in a manner effective to stimulate antibody producing cells. Rodents such as mice and rats are preferred animals, however, the use of rabbit, sheep or frog cells is possible. The use of rats may provide certain advantages, but mice are preferred, with the BALB/c mouse being most preferred as the most routinely used animal and one that generally gives a higher percentage of stable fusions.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer removed. Spleen lymphocytes are obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency and enzyme deficiencies that render then incapable of growing in certain selective media which support the growth of only the desired fused cells, called "hybridomas."

Any one of a number of myeloma cells may be used and these are known to those of skill in the art. For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein *Nature* 256:495–497 (1975) and *Eur. J. Immunol.* 6:511–519 (1976), and those using polyethylene glycol (PEG), such as 37% (v/v) PEG, by Gefter et al. *Somatic Cell Genet.* 3:231–236 (1977). The use of electrically induced fusion methods is also appropriate.

Fusion procedures usually produce viable hybrids at low frequencies, about $1 \times 10^{-6}$ to $1 \times 10^{-8}$. This does not pose a problem, however, as the viable, fused hybrids are differentiated from the parental, unfused cells (particularly the unfused myeloma cells that would normally continue to divide indefinitely) by culture in a selective medium. The selective medium generally is one that contains an agent that blocks the de novo synthesis of nucleotides in the tissue culture media. Exemplary and preferred agents are aminopterin, methotrexate and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas are then serially diluted and cloned into individual antibody-producing cell lines, which clones can then be propagated indefinitely to provide MAbs. The cell lines may be exploited for MAb production in two basic ways. A sample of the hybridoma can be injected, usually in the peritoneal cavity, into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

Monoclonal antibodies of the present invention also include anti-idiotypic antibodies produced by methods well-known in the art. Monoclonal antibodies according to the present invention also may be monoclonal heteroconjugates, i.e., hybrids of two or more antibody molecules. In another embodiment, monoclonal antibodies according to the invention are chimeric monoclonal antibodies. In one approach, the chimeric monoclonal antibody is engineered by cloning recombinant DNA containing the promoter, leader, and variable-region sequences from a mouse anti-PSA producing cell and the constant-region exons from a human antibody gene. The antibody encoded by such a recombinant gene is a mouse-human chimera. Its antibody specificity is determined by the variable region derived from mouse sequences. Its isotype, which is determined by the constant region, is derived from human DNA.

In another embodiment, monoclonal antibodies according to the present invention is a "humanized" monoclonal antibody, produced by techniques well-known in the art. That is, mouse complementary determining regions ("CDRs") are transferred from heavy and light V-chains of the mouse Ig into a human V-domain, followed by the replacement of some human residues in the framework regions of their murine counterparts. "Humanized" monoclonal antibodies in accordance with this invention are especially suitable for use in in vivo diagnostic and therapeutic methods.

As stated above, the monoclonal antibodies and fragments thereof according to this invention can be multiplied according to in vitro and in vivo methods well-known in the art. Multiplication in vitro is carried out in suitable culture media such as Dulbecco's modified Eagle medium or RPMI 1640 medium, optionally replenished by a mammalian serum such as feta calf serum or trace elements and growth-sustaining supplements, e.g., feeder cells, such as normal mouse peritoneal exudate cells, spleen cells, bone marrow macrophages or the like. In vitro production provides relatively pure antibody preparations and allows scale-up to give large amounts of the desired antibodies. Techniques for large scale hybridoma cultivation under tissue culture conditions are known in the art and include homogenous suspension culture, e.g., in an airlift reactor or in a continuous stirrer reactor or immobilized or entrapped cell culture.

Large amounts of the monoclonal antibody of the present invention also may be obtained by multiplying hybridoma cells in vivo. Cell clones are injected into mammals which are histocompatible with the parent cells, e.g., syngeneic mice, to cause growth of antibody-producing tumors. Optionally, the animals are primed with a hydrocarbon, especially oils such as Pristane (tetramethylpentadecane) prior to injection.

In accordance with the present invention, fragments of the monoclonal antibody of the invention can be obtained from monoclonal antibodies produced as described above, by methods which include digestion with enzymes such as pepsin or papain and/or cleavage of disulfide bonds by chemical reduction. Alternatively, monoclonal antibody fragments encompassed by the present invention can be synthesized using an automated peptide synthesizer, or they may be produced manually using techniques well known in the art.

The monoclonal conjugates of the present invention are prepared by methods known in the art, e.g., by reacting a monoclonal antibody prepared as described above with, for instance, an enzyme in the presence of a coupling agent such as glutaraldehyde or periodate. Conjugates with fluorescein markers are prepared in the presence of these coupling agents, or by reaction with an isothiocyanate. Conjugates with metal chelates are similarly produced. Other moieties to which antibodies may be conjugated include radionuclides such as $^3$H, 125I, $^{131}$I $^{32}$P, $^{35}$S, $^{14}$C, $^{51}$Cr, $^{36}$Cl, $^{57}$Co, 58Co, $^{59}$Fe, $^{75}$Se, $^{152}$Eu, and $^{99m}$Tc, are other useful labels which can be conjugated to antibodies. Radioactively labeled monoclonal antibodies of the present invention are produced according to well-known methods in the art. For instance, monoclonal antibodies can be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium-$^{99}$m by ligand exchange process, for example, by reducing pertechnate with stannous solution, chelating the reduced technetium onto a Sephadex column and applying the antibody to this column or by direct labeling techniques, e.g., by incubating pertechnate, a reducing agent such as SNCl$_2$, a buffer solution such as sodium-potassium phthalate solution, and the antibody.

Immunoassays

The anti-PSA antibodies will have significant utility in assays for the detection of the PSA antigen, as needed in diagnosis and prognostic monitoring. Immunoassays encompassed by the present invention include, but are not limited to those described in U.S. Pat. Nos. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and Western blotting, dot blotting, FACS analyses, and the like may also be used.

In one exemplary ELISA, the anti-PSA antibodies of the invention are immobilized onto a selected surface exhibiting protein affinity, such as a well in a polystyrene microtiter plate. Then, a test composition suspected of containing the PSA antigen, such as a clinical sample, is added to the wells. After binding and washing to remove non-specifically bound immune complexes, the bound PSA antigen may be detected. Detection is generally achieved by the addition of another anti-PSA antibody that is linked to a detectable label. This type of ELISA is a simple "sandwich ELISA". Detection may also be achieved by the addition of a second anti-PSA antibody, followed by the addition of a third antibody that has binding affinity for the second anti-PSA antibody, with the third antibody being linked to a detectable label.

In another exemplary ELISA, the samples suspected of containing the PSA antigen are immobilized onto the well surface and then contacted with the anti-PSA antibodies of the invention. After binding and appropriate washing, the bound immune complexes are detected. Where the initial anti-PSA antibodies are linked to a detectable label, the immune complexes may be detected directly. Again, the immune complexes may be detected using a second antibody that has binding affinity for the first anti-PSA antibody, with the second antibody being linked to a detectable label.

Competition ELISAs are also possible in which test samples compete for binding with known amounts of labeled PSA antigens or antibodies. The amount of reactive species in the unknown sample is determined by mixing the sample with the known labelled species before or during incubation with coated wells. The presence of reactive species in the sample acts to reduce the amount of labeled species available for binding to the well and thus reduces the ultimate signal.

Irrespective of the format employed, ELISAs have certain features in common, such as coating, incubating or binding, washing to remove non-specifically bound species, and detecting the bound immune complexes. These are described as below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of the PSA or anti-PSA antibody to the well, coating with a non-reactive material to reduce background, and washing to remove unbound material, the immobilizing surface is contacted with the clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The suitable conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 40° C. or so.

Following all incubation steps in an ELISA, the contacted surface is washed so as to remove non-complexed material. Washing often includes washing with a solution of PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immune complex formation, e.g., incubation for 2 hours at room temperature in a PBS-containing solution such as PBS-Tween.

After incubation with the labeled antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

Alternatively, the label may be a chemilluminescent one. The use of such labels is described in U.S. Pat. Nos. 5,310,687, 5,238,808 and 5,221,605, all of which are incorporated by reference in their entirety.

A typical application of immunoprecipitation involves the use of *Staphylococcus aureus* bacteria that have protein A expressed on the peptidoglycan cell wall. In this method, an antibody that recognizes the antigen of interest is quickly precipitated by the binding of the antibody to the protein A on the cells which are then easily precipitated by centrifugation (Kessler, S. W. *Methods in Enzymology*, 73:442, 1981). Alternatively, protein A-conjugated beads can be used in place of the *S. aureus* bacteria.

Assays for PSA polypeptides also can determine normal/abnormal tissue distribution for diagnostic purposes. Methods for in vitro and in situ analysis are well known and involve assessing binding of PSA-specific antibodies to tissues, cells or cell extracts. These are conventional techniques well within the grasp of those skilled in the art. For example, the antibodies of the present invention may be used in conjunction with both fresh-frozen and formalin-fixed, paraffin-embedded tissue blocks prepared from study by immunohistochemistry (IHC). Each tissue block may consist of 50 mg of residual "pulverized" prostate tumor. The method of preparing tissue blocks from these particulate specimens has been successfully used in previous IHC studies of various prognostic factors, e.g., in breast cancer, and is well known to those of skill in the art. Abbondanzo et al., *Breast Cancer Res. Treat.* 16:182(#151), 1990; Allred et al., *Breast Cancer Res. Treat.* 16:182(#149), 1990; Brown et al., *Breast Cancer Res. Treat.* 16:192(#191), 1990.

Briefly, frozen-sections may be prepared by rehydrating 50 ng of frozen pulverized prostate tumor at room temperature in PBS in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25–50 serial sections containing an average of about 500 remarkably intact tumor cells.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

The invention also relates to an in vivo method of imaging a prostate-derived tumor. Specifically, this method involves administering to a subject an imaging-effective amount of a detectably-labeled anti-PSA monoclonal antibody or fragment thereof and a pharmaceutically-effective carrier and detecting the binding of the labeled monoclonal antibody to the diseased tissue. The term "in vivo imaging" refers to any method which permits the detection of a labeled monoclonal antibody of the present invention or fragment thereof that specifically binds to a target tissue located in the subject's body. A "subject" is a mammal, preferably a human. An "imaging effective amount" means that the amount of the detectably-labeled monoclonal antibody, or fragment thereof, administered is sufficient to enable detection of binding of the monoclonal antibody or fragment thereof to the diseased tissue.

Typically, in vivo imaging relies on radionuclides. A factor to be considered in selecting a radionuclide for in vivo diagnosis is that the half-life must be long enough so that it is still detectable at the time of maximum uptake by the target, but short enough so that deleterious radiation upon the host, as well as background, is minimized. Ideally, a radionuclide used for in vivo imaging will lack a particulate emission, but produce a large number of photons in a 140–2000 keV range, which may be readily detected by conventional gamma cameras.

As discussed above in connection with the production of monoclonal conjugates, a radionuclide may be bound to an antibody either directly or indirectly by using an intermediary functional group. Intermediary functional groups which are often used to bind radioisotopes which exist as metallic ions to antibody are diethylenetriaminepentaacetic acid (DTPA) and ethylene diaminetetracetic acid (EDTA). Examples of metallic ions suitable for use in this invention are $^{99m}$Tc, 123I, 131I $^{111}$In, 131I, $^{97}$Ru, $^{67}$Cu, $^{67}$Ga, 125I, $^{68}$Ga, $^{72}$As, $^{89}$Zr, and $^{201}$Tl.

In accordance with this aspect of the invention, the monoclonal antibody or fragment thereof may be labeled by any of several techniques known to the art. The methods of the present invention also may use paramagnetic isotopes for purposes of in vivo detection. Elements particularly useful in Magnetic Resonance Imaging ("MRI") include $^{157}$Gd, $^{55}$Mn, $^{162}$Dy, $^{52}$Cr, and $^{56}$Fe.

Administration of the labeled antibody may be local or systemic and accomplished intravenously, intraarterially, via the spinal fluid or the like. Administration may also be intradermal or intracavitary, depending upon the body site under examination. After a sufficient time has lapsed for the monoclonal antibody or fragment thereof to bind with the diseased tissue, for example 30 min to 48 h, the area of the subject under investigation is examined by routine imaging techniques such as MRI, SPECT, planar scintillation imaging and emerging imaging techniques, as well. The exact protocol will necessarily vary depending upon factors specific to the patient, as noted above, and depending upon the body site under examination, method of administration and type of label used; the determination of specific procedures would be routine to the skilled artisan. The distribution of the bound radioactive isotope and its increase or decrease with time is then monitored and recorded. By comparing the results with data obtained from studies of clinically normal individuals, the presence and extent of the diseased tissue can be determined.

To test antiserum for the presence of antibodies to an immunodominant motif epitope, an ELISA method is utilized. The peptide segment representing the immunodominant motif epitope is plated in an ELISA microtiter plate well as are other immunosubdominant epitope peptides in separate wells. Antiserum made to an immunodominant epitope will test positive only in the ELISA well in which that epitope peptide is plated and will test negative in wells that contain an epitope peptide segment to which no antibodies are present in the sample. The extent of the homogeneity of sample antibodies for the immunodominant epitope peptide in question can thus be quantitated.

Kits

The PSA peptides and antibodies of the present invention are suitable for use in a kit. Such a kit may comprise a receptacle being compartmentalized to receive one or more containers such as vials, tubes and the like, such containers holding separate elements of the invention. For example, one container may contain a first antibody bound to an insoluble or partly soluble carrier. A second container may contain a soluble, detectably-labeled second antibody, in lyophilized form or in solution. The receptacle may also contain a third container holding a detectably labeled third antibody in lyophilized form or in solution. A kit of this nature can be used in a diagnostic assay according to the invention. Alternatively, the kit may comprise PSA oligopeptides, free or bound to carrier molecules. A second container may contain carrier or adjuvant. A kit of this nature can be used in the production of PSA-specific antibodies.

All of the references mentioned above, to the extent that they provide exemplary procedural or other details supplementary to those set forth herein, are specifically incorporated herein by reference.

EXAMPLES

Example 1—Identification of Immunodominant PSA Epitopes

The amino acid sequence of PSA was divided into fourteen peptide segments. Thirteen of the peptides were 19-mers to 21-mers and one peptide was a 16-mer. Seven of the selected peptides exhibited an antibody immunodominant epitope motif consisting of two descriptors: (1) a proline, usually centrally located, in or at the border of the middle hydrophilic region of sequential amino acids when present, and (2) adjacent hydrophobic-hydrophilic-hydrophobic regions in a linear sequence of from 12–21 amino acids as determined by Kyte-Doolittle hydrophilicity plots. Seven of the peptides displayed both of the descriptors while five of the peptides displayed only the proline descriptors. Two of the peptides lacked both the proline and the hydrophobic-hydrophilic-hydrophobic region descriptors.

The combined presence of the two descriptors correlated extremely well with the immunodominance of PSA peptide segments. The six highest scoring PSA peptides in terms of ELISA activity with anti-whole PSA antibody had both characteristics as did the eighth best. Also, the presence of a central proline in a segment lacking the adjacent hydrophobic, hydrophilic, and hydrophobic region characteristic successfully predicted four of five subdominant (moderately ELISA reactive) epitopes, while the absence of both the proline and the hydrophobic-hydrophilic-hydrophobic region characteristics in a peptide segment correctly predicted the two least ELISA reactive peptide segments. These results substantiate the importance of both defining characteristics in the immunodominance motif and were confirmed in two separate ELISA runs.

Example 2—Reactivity of Anti-PSA MAbs with PSA Peptides

In order to further evaluate the immunodominance of the identified peptides, three anti-PSA monoclonal antibodies were tested for their ELISA reactivity with all fourteen PSA epitope peptide segments. One monoclonal antibody reacted strongly with a PSA peptide segment that displayed both descriptors while the other two monoclonals scored as strong positive and moderate positive, respectively, with another epitope that also displayed both descriptors.

ELISA ACTIVITY RANKINGS OF PROSTATE SPECIFIC ANTIGEN (PSA) EPITOPES
AVERAGE OF "WET" AND "DRY" ELISA METHODS

| RANK | PSA SEQUENCE NUMBER | AMINO ACID SEQUENCE | HYDROPHOBIC-HYDROPHILIC-HYDROPHOBIC | PROLINE |
|---|---|---|---|---|
| 1. | 221–240 | LYTKVVHYRKWIKDTIVANP | YES | YES |
| 2. | 111–130 | AVKVMDLPQEPALGTTCYA | YES | YES |
| 3. | 1–20 | IVGGWECEKHSQPWQVLVAS | YES | YES |
| 4.5. | 163–176 | CAQVHPQKVTKFML | YES | YES |
| 4.5. | 97–115 | YLMLLRLSEPAELTDDAVKVM | YES | YES |
| 6. | 81–100 | LLKNRFLRPGDDSSHDLMLLY | YES | YES |
| 7. | 129–148 | YASGWGSIEPEEHLLYNQMK | NO | YES |

-continued

ELISA ACTIVITY RANKINGS OF PROSTATE SPECIFIC ANTIGEN (PSA) EPITOPES
AVERAGE OF "WET" AND "DRY" ELISA METHODS

| RANK | PSA SEQUENCE NUMBER | AMINO ACID SEQUENCE | HYDROPHOBIC-HYDROPHILIC-HYDROPHOBIC | PROLINE |
|---|---|---|---|---|
| 8. | 49–68 | ILLGRHSLFHPEDTGQVFQVY | YES | YES |
| 9. | 202–221 | LQGITSWGSEPCALPERPSL | NO | YES |
| 10. | 65–84 | VFQVSTSFPHPLYNMSLLKN | NO | YES |
| 11. | 186–204 | YSTCSGDSGGPLVCNGVLQG | NO | YES |
| 12. | 24–41 | YAVCGGVLVHPQWVLTAAH | NO | YES |
| 13. | 37–55 | YLTAAHCIRRSVILLGRHS | NO | NO |
| 14. | 142–161 | LLYDQMKKLQCVQLHVISND | NO | NO |

Reading from the top towards the bottom of column 3, the listed sequences are represented by SEQ ID NO:2 through SEQ ID NO:7, SEQ ID NO:16, SEQ ID NO:8, and SEQ ID NO:18 through SEQ ID NO:22

Example 3—Determining Homogeneity in Anti-PSA(163–176) Sera

Sheep antiserum was raised against the PSA immunodominant linear epitope spanning PSA amino acids 163–176. This epitope was selected since it had both descriptors and also since its sequence was relatively non-homologous with another prostatic kallekrein, known as human glandular kallekrein (HgK).

To test the homogeneity of this PSA antiserum for the peptide amino acid sequence 163–176, PSA peptide 163–176 was plated in duplicate ELISA microtiter plate well rows as were other potential PSA epitope peptides in their respective duplicate ELISA plate rows. The PSA antiserum was serially diluted and added to the entire set of duplicate ELISA well rows.

The antiserum only tested significantly positive in the ELISA well rows that contained the immunogen epitope peptide comprised of PSA linear amino acid sequence 163–176. The titer of the antiserum with this peptide was $4.3 \times 10^6$. While the antiserum did not interact significantly with the other PSA epitope peptides, however, a background titer of between 1,300 and 30,000 was observed. Thus, the specificity of antibodies for PSA amino acid sequence 163–176 was quantitatively verified.

Example 4—PSA Specificity of Anti-PSA(163–176) Sera

The sheep polyclonal sera described in Example 3 further was evaluated in terms of specificity for PSA, as opposed to the related kallikrein HgK. The average ELISA activities of the anti-PSA (163–176) sera tested against the immunogen PSA peptide and HgK were as follows:

anti-PSA (163–176) peptide antibody titer to PSA 9163–176) = 2.965E6
"    "    "    "    "    to E121 HgK epitope= 2.485e4

These data give an E87 PSA epitope:E121 HgK epitope, anti-PSA peptide sera titer ratio of 119:1. This demonstrates that the sera is highly specific for PSA.

Example 5—Antiserum Purification

Antisera raised in sheep to various PSA peptides are used as a source of antibody. This antiserum is affinity purified on a PSA peptide column as follows. The antigen is coupled to Sepharose CL-6B beads (Pharmacia) at approximately 0.5 mg total protein per mg of gel following activation with carbonyldiimidazole in dioxan (0.4 g per ml of gel). Coupling is carried out in 0.5M $Na_2CO_3$, 0.5M NaCl (pH9.5) at 0° C. over two nights. After incubation, the gel is washed alternatively in 0.1M $NaHCO_3$, 0.1M NaCl (pH 8.0) and 0.1M $CH_3.COONa.3H_2O$, 0.1M glycine HCl (pH 4.5) and finally washed with ice-cold 0.1M glycine HCl (pH 2.5). The gel is then neutralized and stored in 0.01M Tris, 0.15M NaCl (pH 8.0).

The antibodies against the PSA peptide are bound to the antigen column in Tris-saline buffer (pH 8.0) and specifically eluted with 0.1M glycine-HCl buffer (pH 2.5). Following elution, the eluant is adjusted to pH 8.0 using 2M Tris. Antibody is concentrated on a YM30 filter and dialyzed into water. Precipitating fats, etc., are removed by centrifugation. The dialyzed antibody solution is then adjusted to 0.1M $NaHCO_3$ 0.5M NaCl (pH 8.3) and incubated overnight at 4° C. with CNBr-activated Sepharose. Unreacted groups are blocked with 1.0M ethanolamine pH 8.0 overnight at 4° C. The Sepharose beads are then washed with 0.1M $NaHCO_3$, 0.5M NaCl (pH 8.3) buffer followed by 0.1M sodium acetate buffer and stored in Tris-saline buffer pH 8.0 containing 0.001% sodium azide as a preservative. The columns are washed with ice-cold 0.1M glycine-HCl buffer (pH 2.5) immediately prior to use to remove any weakly bound antibody.

Example 6—Estimation of Antibody Concentrations

Antibody concentrations are estimated using a direct, non-competitive ELISA. Positive control PSA peptides are diluted in carbonate/bicarbonate buffer pH 9.6 to a final concentration of 1 µg/ml. Aliquots of 200 µl are added to each well of a microtiter plate. Following overnight incubation at 4° C., plates are washed with PBS containing 0.05% (w/v) Tween 20 and blocked with gelatin. The same buffer is used for subsequent coupling and washing steps. Primary antibody is diluted in PBS-Tween 20 and allowed to react for 1 h at 37° C. For the assays with bovine sera, this is followed by incubation with a 1:500 dilution of 0.5 mg/ml peroxidase labelled goat anti-bovine IgG (H+L). For assays of rabbit antisera, reaction with the primary antiserum is followed by a 45 min reaction with a 1:1200 dilution of biotinylated donkey anti-rabbit IgG, then 45 min with 1:1200 peroxidase coupled streptavidin.

Peroxidase activity is measured with 1 mg/ml 5-aminosalicylic acid and 1.7 mM hydrogen peroxide in 20 mM phosphate buffer pH 6.7. Absorbance values are measured using a Titretek Multiscan Plus Mk II ELISA reader interfaced with an IBM compatible personal computer. Data are processed using the Kinetic Linked Immunosorbent Assay (KELA) to yield a kinetic estimate of the peroxidase activity.

Example 7—Production of Monoclonal Antibodies

A preferred embodiment of the present invention is a monoclonal antibody that recognizes the peptide antigens disclosed herein. Means for preparing and characterizing antibodies are well known in the art (See, e.g., *Antibodies "A Laboratory Manual*, E. Howell and D. Lane, Cold Spring Harbor Laboratory, 1988).

To obtain monoclonal antibodies, one would initially immunize an experimental animal, often preferably a mouse, with an antigenic PSA peptide composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to the desired PSA peptide.

Following immunization, spleen cells are removed and fused, using a standard fusion protocol (see, e.g., The Cold Spring Harbor Manual for Hybridoma Development, incorporated herein by reference) with plasmacytoma cells to produce hybridomas secreting monoclonal antibodies against the peptide. Hybridomas which produce monoclonal antibodies to the selected antigens are identified using standard techniques, such as ELISA and Western blot methods.

Hybridoma clones can then be cultured in liquid media and the culture supernatants purified to provide the PSA peptide-specific monoclonal antibodies.

Example 8—The Immunodominant Epitope Motif Specifies Protein Loop Structures in Gelonin A protein loop structure by definition is comprised of a linear sequence of amino acids that originates beneath or at the surface of a protein, loops out into the aqueous environment, and then returns to and may travel beneath the outer surface of the protein. Carlacci and Englander, *BIOPOLYMERS* 33:1271–1286 (1993); Bruccoleri et al., *Nature* 335:564–568 (1988); Fine et al., *PROTEINS: Structure, Function and Genetics* 1:342–362 (1986). It is contemplated that loop formation is facilitated by the two characteristics that define the immunodominant motif presented here: (1) a hydrophobic-hydrophilic-hydrophobic region in a linear sequence of from twelve to twenty amino acids and (2) a proline, usually centrally located in the sequence within or at the border of the middle hydrophilic region. Since the termini defined in the immunodominant motif are hydrophobic, the proposed starting and ending points of the protein loop are comprised of these hydrophobic amino acids and can interact hydrophobically with buried amino acids near the protein surface which most likely are also hydrophobic. The middle hydrophilic region of the immunodominant motif is the proposed location of the loop amino acids which are extended out from the surface of protein proper. These extended, hydrophilic amino acids are biochemically suited to interact with the aqueous environment surrounding proteins. The bend in the amino acid chain at the motif's centrally located proline aids in returning the loop to the protein's surface.

Four peptide segments from the plant protein gelonin that met the requirements of the immunodominant motif to various degrees, were ranked for potential immunodominance. Subsequently, the location of these segments was approximated using a three dimensional ribbon model of gelonin. The three gelonin peptide segments that ranked highest with respect to the immunodominant motif criteria were found to form loop structures in the 3-D ribbon model of gelonin.

---

What is claimed is:

1. A peptide of twelve to twenty-one contiguous amino acid residues from the sequence of SEQ ID NO:1, wherein said peptide is defined by a motif of two hydrophobic and one hydrophilic regions arranged in the following manner:

hydrophobic-hydrophilic-hydrophobic wherein each of said hydrophobic and hydrophilic regions are of about five amino acid residues in length.

2. The peptide according to claim 1, wherein said peptide corresponds to the twenty-one N- or C-terminal residues of the sequence of SEQ ID NO: 1.

3. The peptide according to claim 1, wherein said motif further is defined by a proline residue (i) within said hydrophilic region, (ii) at the border of said hydrophilic region or (iii) at least five amino acid residues from one end of said peptide.

4. The peptide according to claim 1, wherein said peptide further comprises a leucine, isoleucine or lysine residue within one or both of said hydrophobic regions.

5. The peptide according to claim 1, wherein said peptide further is characterized by an approximated 3600 (−)cosine hydrophilicity pattern.

6. The peptide according to claim 1, wherein the amino acid sequence is selected from the group consisting of LYTKVVHYRKWIKDTIVANP (SEQ ID NO:2), AVKVM-DLPQEPALGTTCYA (SEQ ID NO:3), IVGGWECEKH-SQPWQVLVAS (SEQ ID NO:4), CAQVHPQKVTKFML (SEQ ID NO:5), YLMLLRLSEPAELTDDAVKVM (SEQ ID NO:6), LLKNRFLRPGDDSSHDLMLLY (SEQ ID NO:7), and ILLGRHSLFHPEDTGQVFQVY (SEQ ID NO 8).

7. The peptide according to claim 6, wherein the peptide sequence is CAQVHPQKVTKFML (SEQ ID NO:5).

8. A peptide that is a variant of a peptide having the amino acid sequence selected from the group consisting of LYTKVVHYRKWIKDTIVANP (SEQ ID NO:2), AVKVM-DLPQEPALGTTCYA (SEQ ID NO:3), IVGGWECEKH-SQPWQVLVAS (SEQ ID NO:4), CAQVHPQKVTKFML (SEQ ID NO:5), YLMLLRLSEPAELTDDAVKVM (SEQ ID NO:6), LLKNRFLRPGDDSSHDLMLLY (SEQ ID NO:7), and ILLGRHSLFHPEDTGQVFQVY (SEQ ID NO:8), wherein said variant has one, two, three, four or five residues that are conservative variations of the selected sequence.

9. An antigenic composition comprising the peptide of claim 1 and a carrier molecule.

10. The antigenic composition according to claim 9, further comprising an adjuvant.

* * * * *

UNITED STATES PATENT AND TRADEMARK OFFICE
CERTIFICATE OF CORRECTION

PATENT NO. : 5,807,978
DATED : September 15, 1998
INVENTOR(S) : William J. Kokolus et al It is certified that error appears in the above-identified patent and that said Letters Patent is hereby corrected as shown below:

Column 35, line 28, numeral "3600" should read -360°-.

Signed and Sealed this

Eighth Day of December, 1998

Attest:

BRUCE LEHMAN

Attesting Officer    Commissioner of Patents and Trademarks

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
       ( A ) LENGTH: 240 amino acids
       ( B ) TYPE: amino acid
       ( C ) STRANDEDNESS: single
       ( D ) TOPOLOGY: linear ( i i ) MOLECULE TYPE: protein ( x i ) SEQUENCE DESCRIPTION: SEQ ID NO:1:

```
Ile Val Gly Gly Trp Glu Cys Glu Lys His Ser Gln Pro Trp Gln Val
 1               5                  10                  15

Leu Val Ala Ser Arg Gly Arg Ala Val Cys Gly Gly Val Leu Val His
                20                  25                  30

Pro Gln Trp Val Leu Thr Ala Ala His Cys Ile Arg Arg Lys Ser Val
            35                  40                  45

Ile Leu Leu Gly Arg His Ser Leu Phe His Pro Glu Asp Thr Gly Gln
        50                  55                  60

Val Phe Gln Val Ser Thr Ser Phe Pro His Pro Leu Tyr Asp Met Ser
```

```
             65                      70                     75                     80
     Leu Leu Lys Asn Arg Phe Leu Arg Pro Gly Asp Asp Ser Ser His Asp
                     85                  90                  95

Leu Met Leu Leu Arg Leu Ser Glu Pro Ala Glu Leu Thr Asp Ala Val
                 100                 105                 110

Lys Val Met Asp Leu Pro Thr Gln Glu Pro Ala Leu Gly Thr Thr Cys
             115                 120                 125

Tyr Ala Ser Gly Trp Gly Ser Ile Glu Pro Glu Glu His Leu Leu Tyr
         130             135                 140

Asp Gln Met Lys Lys Leu Gln Cys Val Gln Leu His Val Ile Ser Asn
     145             150                 155                     160

Asp Val Cys Ala Gln Val His Pro Gln Lys Val Thr Lys Phe Met Leu
                     165             170              175

Cys Ala Gly Arg Trp Thr Gly Gly Lys Ser Thr Cys Ser Gly Asp Ser
                 180                 185             190

Gly Gly Pro Leu Val Cys Asn Gly Val Leu Gln Gly Ile Thr Ser Trp
             195             200                 205

Gly Ser Glu Pro Cys Ala Leu Pro Glu Arg Pro Ser Leu Tyr Thr Lys
         210             215              220

Val Val His Tyr Arg Lys Trp Ile Lys Asp Thr Ile Val Ala Asn Pro
     225             230              235                     240
```

( 2 ) INFORMATION FOR SEQ ID NO:2:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
     Leu Tyr Thr Lys Val Val His Tyr Arg Lys Trp Ile Lys Asp Thr Ile
     1               5                   10                  15

Val Ala Asn Pro
                 20
```

( 2 ) INFORMATION FOR SEQ ID NO:3:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
     Ala Val Lys Val Met Asp Leu Pro Gln Glu Pro Ala Leu Gly Thr Thr
     1               5                   10                  15

Cys Tyr Ala
```

( 2 ) INFORMATION FOR SEQ ID NO:4:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide (xi) SEQUENCE DESCRIPTION: SEQ ID NO:4:

Ile Val Gly Gly Trp Glu Cys Glu Lys His Ser Gln Pro Trp Gln Val
1               5                   10                  15

Leu Val Ala Ser
            20

(2) INFORMATION FOR SEQ ID NO:5:

(i) SEQUENCE CHARACTERISTICS:
      (A) LENGTH: 14 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:5:

Cys Ala Gln Val His Pro Gln Lys Val Thr Lys Phe Met Leu
1               5                   10

(2) INFORMATION FOR SEQ ID NO:6:

(i) SEQUENCE CHARACTERISTICS:
      (A) LENGTH: 21 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:6:

Tyr Leu Met Leu Leu Arg Leu Ser Glu Pro Ala Glu Leu Thr Asp Asp
1               5                   10                  15

Ala Val Lys Val Met
            20

(2) INFORMATION FOR SEQ ID NO:7:

(i) SEQUENCE CHARACTERISTICS:
      (A) LENGTH: 21 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:7:

Leu Leu Lys Asn Arg Phe Leu Arg Pro Gly Asp Asp Ser Ser His Asp
1               5                   10                  15

Leu Met Leu Leu Tyr
            20

(2) INFORMATION FOR SEQ ID NO:8:

(i) SEQUENCE CHARACTERISTICS:
      (A) LENGTH: 21 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:8:

Ile Leu Leu Gly Arg His Ser Leu Phe His Pro Glu Asp Thr Gly Gln
1               5                   10                  15

Val Phe Gln Val Tyr
            20

( 2 ) INFORMATION FOR SEQ ID NO:9:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Asn  Pro  Asp  Val  Lys
 1                    5
```

( 2 ) INFORMATION FOR SEQ ID NO:10:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Thr  Ile  Asn  Lys  Glu  Asp  Asp  Glu  Ser  Pro  Gly  Leu  Tyr  Gly
 1                    5                             10
```

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Thr  Ile  Asn  Lys  Glu  Asp
 1                    5
```

( 2 ) INFORMATION FOR SEQ ID NO:12:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Thr  Ile  Asn  Lys  Glu
 1                    5
```

( 2 ) INFORMATION FOR SEQ ID NO:13:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Thr  Ile  Asn  Lys  Glu  Asp  Asp  Glu  Ser  Pro  Gly
 1                    5                             10
```

( 2 ) INFORMATION FOR SEQ ID NO:14:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Asn  Lys  Glu  Asp  Asp  Glu  Ser
 1                   5
```

( 2 ) INFORMATION FOR SEQ ID NO:15:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
Val  Gly  Glu  Ile  Ala  Ser  Lys  Val  Asp  Pro  Asn  Lys  Ile  Leu
 1                   5                        10
```

( 2 ) INFORMATION FOR SEQ ID NO:16:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Tyr  Ala  Ser  Gly  Trp  Gly  Ser  Ile  Glu  Pro  Glu  Glu  His  Leu  Leu  Tyr
 1                   5                        10                        15
Asn  Gln  Met  Lys
              20
```

( 2 ) INFORMATION FOR SEQ ID NO:17:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Leu  Gln  Gly  Ile  Thr  Ser  Trp  Gly  Ser  Glu  Pro  Cys  Ala  Leu  Pro  Glu
 1                   5                        10                        15
Arg  Pro  Ser  Leu
              20
```

( 2 ) INFORMATION FOR SEQ ID NO:18:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

Val Phe Gln Val Ser Thr Ser Phe Pro His Pro Leu Tyr Asn Met Ser
1               5                   10                  15

Leu Leu Lys Asn
            20

( 2 ) INFORMATION FOR SEQ ID NO:19:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

Tyr Ser Thr Cys Ser Gly Asp Ser Gly Pro Leu Val Cys Asn Gly
1               5                   10                  15

Val Leu Gln Gly
            20

( 2 ) INFORMATION FOR SEQ ID NO:20:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

Tyr Ala Val Cys Gly Gly Val Leu Val His Pro Gln Trp Val Leu Thr
1               5                   10                  15

Ala Ala His ( 2 ) INFORMATION FOR SEQ ID NO:21:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

Tyr Leu Thr Ala Ala His Cys Ile Arg Arg Ser Val Ile Leu Leu Gly
1               5                   10                  15

Arg His Ser ( 2 ) INFORMATION FOR SEQ ID NO:22:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

Leu Leu Tyr Asp Gln Met Lys Lys Leu Gln Cys Val Gln Leu His Val
1               5                   10                  15

Ile Ser Asn Asp
20